United States Patent [19]

Fuchikami et al.

[11] Patent Number: 5,182,246
[45] Date of Patent: Jan. 26, 1993

[54] CATALYST FOR HYDROGENATION, DEHYDROSILYLATION OR HYDROSILYLATION AND USE THEREOF

[75] Inventors: Takamasa Fuchikami, Kanagawa; Yumiko Ubukata, Tokyo, both of Japan; Yasutaka Tanaka, Strasbourg, France

[73] Assignee: Sagami Chemical Research Center, Tokyo, Japan

[21] Appl. No.: 752,646

[22] PCT Filed: Dec. 26, 1990

[86] PCT No.: PCT/JP90/01708
§ 371 Date: Aug. 23, 1991
§ 102(e) Date: Aug. 23, 1991

[87] PCT Pub. No.: WO91/09674
PCT Pub. Date: Jul. 11, 1991

[30] Foreign Application Priority Data

Dec. 26, 1989 [JP] Japan .................. 1-335207
Aug. 6, 1990 [JP] Japan .................. 2-206879
Aug. 6, 1990 [JP] Japan .................. 2-206880
Aug. 6, 1990 [JP] Japan .................. 2-206881

[51] Int. Cl.⁵ .......................................... B01J 31/20
[52] U.S. Cl. ........................ 502/161; 502/164; 556/470; 556/481
[58] Field of Search ........................... 502/161, 164

[56] References Cited

U.S. PATENT DOCUMENTS

| | | | |
|---|---|---|---|
| 3,849,513 | 11/1974 | Doyle | 260/683 |
| 3,859,359 | 1/1975 | Keblys | 260/604 |
| 3,894,089 | 7/1975 | Farona et al. | 260/591 |
| 3,954,665 | 5/1976 | Tkatchenko | 502/161 |
| 4,190,609 | 2/1980 | Lin | 502/161 X |
| 4,331,811 | 5/1982 | Werner et al. | 546/345 |
| 4,361,497 | 11/1982 | Boldt et al. | 502/159 |
| 4,514,380 | 4/1985 | Hunter | 423/417 |

Primary Examiner—Patrick P. Garvin
Attorney, Agent, or Firm—Nixon & Vnaderhye P.C.

[57] ABSTRACT

A catalyst for hydrogenation, dehydrosilylation of ketones, or hydrosililation of dienes or acetylenes, comprising a complex represented the the formula:

$$A^+[M_2H(C))_{10}]^-$$

wherein $A^+$ represents an alkali metal cation, an ammonium cation, an iminium cation, or a phosphonium cation; and M represents a chromium atom, a molybdenum atom, or a tungsten atom; and a process for producing dehydrosilylation products of ketones or hydrosilylation products of dienes or acetylenes, which is characterized by using the complex as a catalyst.

1 Claim, No Drawings

CATALYST FOR HYDROGENATION, DEHYDROSILYLATION OR HYDROSILYLATION AND USE THEREOF

FIELD OF THE INVENTION

This invention relates to a catalyst useful for hydrogenation, dehydrosilylation of ketones, and hydrosilylation of dienes or acetylenes and to a process for carrying out these reactions using the same.

BACKGROUND OF THE INVENTION

A number of compounds which catalyze a hydrogenation reaction are known (refer to *SHIN JIKKEN KAGAKU KOZA* 15, *SANKA TO KANGEN (II)*, Maruzen (1977)). These catalysts can be roughly divided into homogeneous catalysts and heterogeneous catalysts.

In heterogeneous hydrogenation reaction, a reactant is generally used in a gaseous phase, and applicable reaction substances are therefore limited. Besides, since high reaction temperature are required, the reaction substance is apt to decompose thus producing by-products. Further, heterogeneous catalysts for hydrogenation have lower selectivity than homogeneous catalysts for hydrogenation.

On the other hand, catalysts comprising the group VIII transition metals, such as rhodium, platinum, and ruthenium, are well known for homogeneous hydrogenation, but these metals are extremely expensive and therefore economically disadvantageous.

In addition, the above-mentioned catalysts are disadvantageous in that they not only catalyze hydrogenation but induce hydrogenolysis of a carbon-halogen bond, etc.

In order to overcome these disadvantages, there have been proposed complexes of the group VIB metals, e.g., chromium, molybdenum, and tungsten, such as arene-chromium tricarbonyl and bis(tricarbonylcyclopentadienylchromium). However, these complexes exhibit activity only on hydrogenation of cissoid dienes or acetylenes. Moreover, they must be used in a large quantity due to their low catalyst activity and still require high temperature and high pressure conditions for accomplishing the desired reaction. Thus, there are great difficulties in applying these complexes to industrial use (see Comparative Examples 1 to 5 hereinafter described).

Silyl ethers, allyl silanes, and vinyl silanes are all very important key substances in industry (see, for example, W. P. Weber, *Silicon Reagents for Organic Synthesis*, Springer-Verlag (1983)).

Conventionally known catalysts and processes for directly producing silyl enol ethers from carbonyl compounds and hydrosilanes include (1) a process comprising reacting a hydrosilane with a carbonyl compound having an electron attracting group at the α-position thereof, e.g., acetylacetone and methyl aceto-acetate, using a Wilkinson complex $(Rh(PPh_3)_3Cl)$ as a catalyst (see I. Ojima, M. Nihonyanagi, T. Kogure, M. Kumagai, S. Horiuchi, and K. Nakatsugawa, *J. Organomet. Chem.*, Vol. 94, p. 449 (1975)) and (2) a process comprising reacting cyclohexanone and trimethylsilane using triethylamine as a base and cobalt octacarbonyl as a catalyst (see, H. Sakurai, K. Miyoshi, and Y. Nakadaira, *Tetrahedron Lett.*, 2671 (1977)).

According to the former process using a Wilkinson complex as a catalyst, it is essential for selective progress of dehydrosilylation that the substrate should have an electron attracting group at the α-position thereof, thus narrowly limiting the applicable substrate in kind. The latter process also has a disadvantage such that a substrate to be used must be chosen taking into consideration side reactions arising from the co-existing strong base, e.g., aldol condensation. Further, both reactions are economically disadvantageous because of the use of complexes of expensive metals of the group VIII and entail great difficulties in industrial application (see Reference Examples hereinafter described).

Known catalysts and processes for directly producing allyl silanes from dienes and hydrosilanes include a process in which a complex of the group VIII transition metal, e.g., platinum, palladium, and rhodium, is used and a process utilizing an photochemical reaction with the aid of a chromium hexacarbonyl catalyst (refer, e.g., to S. Patai and Z. Pappoport (ed.), *The Chemistry of Organic Silicon Compounds* (1989)). Reactions using these catalysts, however, are often attended by by-production of a homoallyl silane as a result of progress of 1,2-addition reaction or of a disilylalkane as a result of 1:2 addition reaction, thereby giving a complicated mixture. In using assymetric dienes, these catalysts are hardly applicable t industrial production because the resulting reaction mixture contains positional isomers. Further, uneconomic to use expensive group VIII metal complexes as a catalyst and to use an apparatus for photochemical reaction, making it difficult to adopt these reactions from the standpoint of economy.

Known catalysts and processes for directly producing vinyl silanes from acetylenes and hydrosilanes include a process of using a complex catalyst of the group VIII transition metal, e.g., platinum, palladium, and rhodium, similarly to the above-described processes for producing allyl silanes (see, for example, *The Chemistry of Organic Silicon Compounds, supra*). Where these catalysts are used, the resulting vinyl silane products are mixtures of stereo isomers sometimes containing a disilylalkane that is a 1:2 addition product, thereby providing complicated mixtures. In the case of using assymetic acetylenes, the resulting mixture further contains positional isomers. Therefore, these processes are unsuitable for industrial application.

DISCLOSURE OF THE INVENTION

The present invention provides a cheap industrial catalyst with which the above-described various drawbacks associated with conventional catalysts can be overcome. The present invention also provides a technique of applying such a catalyst to hydrogenation, dehydrosilylation of ketones, and hydrosilylation of dienes or acetylenes to obtain desired products.

The present invention relates to a catalyst comprising a complex represented by formula (I):

$$A^+[M_2(CO)_{10}]^- \qquad (I)$$

wherein $A^+$ represents an alkali metal cation, an ammonium cation, an iminium cation, or a phosphonium cation; and M represents a chromium atom, a molybdenum atom, or a tungsten atom.

The complex represented by formula (I) can be prepared by known processes (see, for example, R. J. Hayter, *J. Am. Chem. Soc.*, Vol. 88, p. 4376 (1966)). From the viewpoint of reaction efficiency and yield, the ammonium cation is preferably a quaternary ammonium cation; the iminium cation is preferably a diphosphine iminium cation; and the phosphonium cation is preferably a quaternary phosphonium cation. The amount of the catalyst to be used is usually selected from the range of from 1/5000 to ½ equivalent to a starting material, though varying depending on the kind and number of starting materials on which the catalyst is to act. For adjustment of catalyst activity or for achieving asymmetric reaction in hydrogenation, a so-called catalytic amount of a tertiary phosphine compound or an acid may be added without any problem. In using a tertiary phosphine compound, it is well known that a part of ligands of the complex are exchanged thereby so that a complex containing a tertiary phosphine as a part of its ligands which is separately prepared may be used.

Hydrogenation reaction using the catalyst according to the present invention is usually carried out in a solvent. While other reactions may be used without a solvent, solvents inert to the reaction are used to advantage. In view of reaction rate, yield, etc., particularly preferred solvents are polar solvents, e.g., diethyl ether, tetrahydrofuran, dimethoxyethane, and dioxane.

The reactions generally proceed at temperatures of from 0° to 150° C. Reaction temperatures of from room temperature to 130° C. are preferred from the standpoint of reaction efficiency, economy, and safety.

The catalysts of the present invention are useful for hydrogenation of an unsaturated bond of compounds. Illustrative examples of compounds which can be hydrogenated by using the catalyst of the invention are those having a carbon-oxygen double bond, e.g., diketones and keto esters; those having a carbon-carbon double bond, e.g., alkenes, dienes, and polyenes; those having a carbon-carbon triple bond, e.g., alkynes, diynes, and polyynes; those having a carbon-nitrogen double bond, e.g., imines and oximes; and those having a carbon-nitrogen triple bond, e.g., nitriles. Where the compound to be hydrogenated has two or more unsaturated bonds which may be the same or different per molecule, the reaction generally proceeds so that a part or all of the unsaturated bonds are hydrogenated. The degree of such reaction progress is sometimes controllable by appropriate selection of reaction temperature, reaction time, and the amount of the catalyst to be used.

Hydrogenation reaction is carried out in the presence of hydrogen. Hydrogen pressure may be applied to accelerate the reaction.

Where the catalyst of the present invention is used for dehydrosilylation of ketones, the reaction can be effected as illustrated below.

A ketone represented by formula (II):

(II)

wherein $R^1$ represents a substituted or unsubstituted alkyl group, a substituted or unsubstituted alkenyl group, or a substituted or unsubstituted aromatic group; and $R^2$ and $R^3$ each represent a hydrogen atom, a substituted or unsubstituted alkyl group, a substituted or unsubstituted alkenyl group or a substituted or unsubstituted aromatic group; provided that a pair or $R^1$ and $R^2$, a pair of $R^1$ and $R^3$, or a pair of $R^2$ and $R^3$ may be taken together to form a ring, and a hydrosilane represented by formula (III):

$$H_2SiR^4R^5 \qquad (III)$$

wherein $R^4$ and $R^5$ each represent a substituted or unsubstituted alkyl group, a substituted or unsubstituted alkenyl group, or a substituted or unsubstituted aromatic group, are reacted in the presence of the complex catalyst of formula (I) to prepare a silyl enol ether represented by formula (IV):

(IV)

wherein $R^1$, $R^2$, $R^3$, $R^4$, and $R^5$ are as defined above.

The ketones of formula (II) and hydrosilanes of formula (III) are easily available in industry. The alkyl group is preferably an alkyl group having from 1 to 10 carbon atoms which may have a branched or cyclic structure, e.g., methyl, ethyl, propyl, butyl, pentyl, hexyl, heptyl, octyl, nonyl, and decyl groups. The alkenyl group is preferably an alkenyl group having from 1 to 10 carbon atoms which may have a branched or cyclic structure, e.g., vinyl, styryl, 1-propenyl, allyl, butenyl, pentenyl, hexenyl, heptenyl, octenyl, decenyl, cyclohexenyl, methallyl, and cinnamyl groups. The aromatic group includes an aromatic hydrocarbon group and a heterocyclic aromatic group. The aromatic hydrocarbon group includes mono- to tetracyclic groups, e.g., phenyl, naphthyl, and anthryl groups. The heterocyclic aromatic group includes mono- to tetracyclic groups containing a nitrogen atom, an oxygen atom, or a sulfur atom, e.g., pyridyl, furyl, and thienyl groups. Examples of substituents for these groups are an alkyl group having from 1 to 10 carbon atoms which may have a branched or cyclic structure, an alkoxy group having from 1 to 10 carbon atoms which may have a branched or cyclic structure, an acyl group, a cyano group, a nitro group, a halogen atom, a phenyl group, a protected or unprotected hydroxyl group, a protected or unprotected amino group, a protected or unprotected carboxyl group, and a protected or unprotected amido group.

Examples of the ketones of formula (II) wherein $R^1$ and $R^2$ or $R^3$ are taken together to form a ring include compounds having a cyclic skeleton composed of 4 to 8 carbon atoms, e.g., a cyclopentanone ring, a cyclohexanone ring, a cycloheptanone ring, a cyclopentanone ring, a cyclohexenone ring, and a cycloheptenone ring. Examples of those wherein $R^2$ and $R^3$ are taken together to form a ring include compounds having a ring composed of 4 to 8 carbon atoms, e.g., a cyclopropane ring, a cyclopentane ring, a cyclohexane ring, a cycloheptane ring, a cyclooctane ring, a cyclopentene ring, a cyclohexene ring, and a cycloheptene ring.

Hydrosilylation of dienes using the catalyst of the present invention can be effected as follows.

A diene represented by formula (V):

$$R^6R^7C=CR^8R^9=CR^{10}R^{11} \qquad (V)$$

wherein $R^6$, $R^7$, $R^8$, $R^9$, $R^{10}$, and $R^{11}$ each represent a hydrogen atom, a substituted or unsubstituted alkyl group, a substituted or unsubstituted alkenyl group, or a substituted or unsubstituted aromatic group; provided that any two of them may be taken together to form a ring, and a hydrosilane represented by formula (VI):

$$HSiR^{12}R^{13}R^{14} \qquad (VI)$$

wherein $R^{12}$, $R^{13}$, and $R^{14}$ each represent a hydrogen atom, a halogen atom, a substituted or unsubstituted alkyl group, a substituted or unsubstituted alkoxy group, a substituted or unsubstituted alkenyl group, or a substituted or unsubstituted aromatic group, are reacted in the presence of the complex catalyst of formula (I) to prepare an allyl silane represented by formula (VII):

$$R^6R^7CHCR^8=CR^9CR^{10}R^{11}SiR^{12}R^{13}R^{14} \qquad (VII)$$

wherein $R^6$, $R^7$, $R^8$, $R^9$, $R^{10}$, $R^{11}$, $R^{12}$, $R^{13}$, and $R^{14}$ are as defined above.

The dienes of formula (V) and hydrosilanes of formula (VI) are easily available in industry. The alkyl group is preferably an alkyl group having from 1 to 10 carbon atoms which may have a branched or cyclic structure, e.g., methyl, ethyl, propyl, butyl, pentyl, hexyl, heptyl, octyl, nonyl, and decyl groups. The alkoxy group is preferably an alkoxy group having from 1 to 10 carbon atoms which may have a branched or cyclic structure, e.g., methoxy, ethoxy, propoxy, butoxy, pentyloxy, hexyloxy, heptyloxy, octyloxy, nonyloxy, and decyloxy groups. The alkenyl group is preferably an alkenyl group having from 1 to 10 carbon atoms which may have a branched or cyclic structure, e.g., vinyl, styryl, 1-propenyl, allyl, butenyl, pentenyl, hexenyl, heptenyl, octenyl, decenyl, cyclohexenyl, methallyl, and cinnamyl groups. The aromatic group includes an aromatic hydrocarbon group and a heterocyclic aromatic group. The aromatic hydrocarbon group includes mono- to tetracyclic groups, e.g., phenyl, naphthyl, and anthryl groups. The heterocyclic aromatic group includes mono- to tetracyclic groups containing a nitrogen atom, an oxygen atom, or a sulfur atom, e.g., pyridyl, furyl, and thienyl groups. Examples of substituents for these groups are an alkyl group having from 1 to 10 carbon atoms which may have a branched or cyclic structure, an alkoxy group having from 1 to 10 carbon atoms which may have a branched or cyclic structure, an acyl group, a cyano group, a nitro group, a halogen atom, a phenyl group, a protected or unprotected hydroxyl group, a protected or unprotected amino group, a protected or unprotected carboxyl group, and a protected or unprotected amino group. Examples of the dienes of formula (V) wherein any two of $R^6$, $R^7$, $R^8$, $R^9$, $R^{10}$, and $R^{11}$ are taken together to form a ring include those having, as a skeleton, a cyclopentadiene ring, a cyclohexadiene ring, a cycloheptadiene ring, a cyclooctadiene ring, a vinylcyclopentene ring, a vinylcyclohexene ring, a vinylcycloheptene ring, or a vinylchclooctene ring.

Hydrosilylation of acetylenes using the catalyst of the present invention can be effected as follows.

An acetylene represented by formula (VIII)

$$R^{15}C\equiv CR^{16} \qquad (VIII)$$

wherein $R^{15}$ and $R^{16}$ each represent a hydrogen atom, a substituted or unsubstituted alkyl group, a substituted or unsubstituted alkenyl group, or a substituted or unsubstituted aromatic group, and a hydrosilane represented by formula (IX):

$$HSiR^{17}R^{18}R^{19} \qquad (IX)$$

wherein $R^{17}$, $R^{18}$, and $R^{19}$ each represent a hydrogen atom, a halogen atom, a substituted or unsubstituted alkyl group, a substituted or unsubstituted alkoxy group, a substituted or unsubstituted alkenyl group, or a substituted or unsubstituted aromatic group, are reacted in the presence of the complex catalyst of formula (I) to prepare an vinyl silane represented by formula (X):

$$R^{15}CH=CR^{16}SiR^{17}R^{18}R^{19} \qquad (X)$$

wherein $R^{15}$, $R^{16}$, $R^{17}$, $R^{18}$, and $R^{19}$ are as defined above.

The acetylenes of formula (VIII) and hydrosilanes of formula (IX) are easily available in industry. The alkyl group is preferably an alkyl group having from 1 to 10 carbon atoms which may have a branched or cyclic structure, e.g., methyl, ethyl, propyl, butyl, pentyl, hexyl, heptyl, octyl, nonyl, and decyl groups. The alkoxy group is preferably an alkoxy group having from 1 to 10 carbon atoms which may have a branched or cyclic structure, e.g., methoxy, ethoxy, propoxy, butoxy, pentyloxy, hexyloxy, heptyloxy, octyloxy, nonyloxy, and decyloxy groups. The alkenyl group is preferably an alkenyl group having from 1 to 10 carbon atoms which may have a branched or cyclic structure, e.g., vinyl, styryl, 1-propenyl, allyl, butenyl, pentenyl, hexenyl, heptenyl, octenyl, decenyl, cyclohexenyl, methallyl, and cinnamyl groups. The aromatic group includes an aromatic hydrocarbon group and a heterocyclic aromatic group. The aromatic hydrocarbon group includes mono- to tetracyclic groups, e.g., phenyl, naphthyl, and anthryl groups. The heterocyclic aromatic group includes mono- to tetracyclic groups containing a nitrogen atom, an oxygen atom, or a sulfur atom, e.g., pyridyl, furyl, and thienyl groups. Examples of substituents for these groups are an alkyl group having from 1 to 10 carbon atoms which may have a branched or cyclic structure, an alkoxy group having from 1 to 10 carbon atoms which may have a branched or cyclic structure, an acyl group, a cyano group, a nitro group, a halogen atom, a phenyl group, a protected or unprotected hydroxyl group, a protected or unprotected amino group, a protected or unprotected carboxyl group, and a protected or unprotected amino group.

The present invention is now illustrated in greater detail with reference to Examples, Reference Examples, and Comparative Examples.

REFERENCE EXAMPLE 1

Synthesis of Tetraethylammonium μ-Hydridebis(pentacarbonylchromium)

$$Cr(CO)_6 + NaBH_4 \rightarrow Na^+[Cr_2H(CO)_{10}]^-$$
$$\rightarrow Et_4N^+[Cr_2H(CO)_{10}]^-$$

Ten milliliters of a tetrahydrofuran (THF) solution containing 2.0 g (9.08 mmol) of chromium hexacarbonyl and 0.20 g (5.28 mmol) of sodium borohydride was refluxed in an argon atmosphere for 18 hours. The reaction mixture was filtered through Celite, and the filtrate was freed of the solvent by distillation under reduced pressure to obtain an orange-red oily substance. To the residue was added 40 ml of ethanol, and 10 ml of an ethanol solution of 0.96 g (4.56 mmol) of tetraethylammonium bromide was added thereto. Immediately thereupon, a yellow crystal began to precipitate. To complete crystallization, the system was allowed to stand in a freezer overnight. The resulting crystal was collected by filtration, dissolved in acetone, and subjected to silica gel column chromatography. The eluent was concentrated, and the precipitated crystal was collected by filtration and dried in vacuo to obtain 1.6 g (70%) of a yellow prism crystal.

Decomposition point: 74°–76° C.

IR (KBr disk) $\nu_{c=0}$: 2040 cm$^{-1}$, 1923 cm$^{-1}$, 1865 cm$^{-1}$, $^1$H-NMR (acetone-d$_6$): δ −19.46 (s, Cr-H-Cr, 1H), 1.27 (t, —CH$_3$, 12H), 3.32 (q, —CH$_2$—, 8H)

A molybdenum complex and a tungsten complex were synthesized in the same manner as described above, except for replacing chromium hexacarbonyl with molybdenum hexacarbonyl and tungsten hexacarbonyl, respectively, and changing the reaction time to 4 hours and 16 hours, respectively. There were obtained 1.8 g (77%) of a molybdenum complex as a pale green prism crystal and 1.3 g (69%) of a tungsten complex as a white prism crystal.

Molybdenum Complex Et$_4$N$^+$[Mo$_2$H(CO)$_{10}$]$^-$:
Decomposition point: 89°–91° C.

IR (KBr disk) $\nu_{c=0}$: 2050 cm$^{-1}$, 1922 cm$^{-1}$, 1865 cm$^{-1}$, $^1$H-NMR (acetone-d$_6$): δ −12.5 (s, Mo—H—Mo, 1H), 1.43 (t, —CH$_3$, 12H), 3.52 (q, —CH$_2$—, 8H)

Tungsten Complex Et$_4$N$^+$[W$_2$H(CO)$_{10}$]$^-$:
Decomposition point: 91°–93° C.

IR (KBr disk) $\nu_{c=0}$: 2050 cm$^{-1}$, 1920 cm$^{-1}$, 1865 cm$^{-1}$, $^1$H-NMR (acetone-d$_6$): δ −12.53 (s, W—H—W, 1H), 1.40 (t, —CH$_3$, 12H), 3.47 (q, —CH$_2$—, 8H)

REFERENCE EXAMPLE 2

Synthesis of Tetrabutylammonium μ-Hydridebis(pentacarbonylchromium)

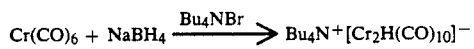

The titled complex was synthesized in the same manner as in Reference Example 1. Five milliliters of a THF solution containing 1.0 g (4.54 mmol) of chromium hexacarbonyl and 0.10 g (2.64 mmol) of sodium borohydride was refluxed in an argon atmosphere for 18 hours. The reaction mixture was filtered through Celite, and the filtrate was freed of the solvent by distillation under reduced pressure to obtain an orange-red oily substance. To the residue was added 20 ml of ethanol, and 5.0 ml of an ethanol solution containing 0.73 g (2.27 mmol) of tetraethylammonium bromide was further added thereto. After allowing the mixture to stand overnight, the solvent was removed by distillation, and the residue was purified by silica gel column chromatography (eluent: chloroform) to obtain 0.55 g (42%) of a yellow prism crystal. The product gradually decomposed in air at room temperature.

IR (KBr disk) $\nu_{c=0}$: 1965 cm$^{-1}$, 1920 cm$^{-1}$, 1875 cm$^{-1}$, $^1$H-NMR (chloroform-d): −19.23 (s, Cr—H—Cr, 1H), 0.13–2.41 (m, —CH$_2$CH$_2$CH$_3$, 28H), 3.71 (q, N—CH$_2$—, 8H)

A bis(triphenylphosphine)iminium complex was synthesized in the same manner, except for replacing tetrabutylammonium bromide with bis(triphenylphosphine)iminium chloride (1.30 mg, 2.27 mmol). There were obtained 1.42 g (75%) of an orange prism crystal.

IR (KBr disk) $\nu_{c=0}$: 1970 cm$^{-1}$, 1940 cm$^{-1}$, 1880 cm$^{-1}$, $^1$H-NMR (chloroform-d): −19.37 (s, Cr—H—Cr, 1H), 7.01–7.91 (m, —C$_6$H$_5$, 20H)

EXAMPLE 1

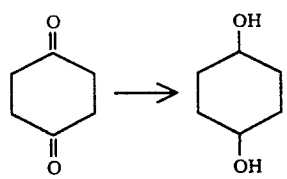

In 1.0 ml of DME, 1.0 mmol of 1,4-cyclohexanedione and 0.01 mmol of tetraethylammonium μ-hydride-bis(pentacarbonylchromium (O)) were heated at 100° C. for 60 hours at a hydrogen pressure of 50 atm while being stirred. GLC analysis of the reaction mixture revealed that 1,4-cyclohexanediol was produced in a yield of 100%.

COMPARATIVE EXAMPLE 1

In 1.0 ml of DME, 1.0 mmol of 1,4-cyclohexanedione and 0.02 mmol of benzenechromium tricarbonyl were heated at 100° C. at a hydrogen pressure of 50 atm for 60 hours while being stirred. GLC analysis of the reaction mixture revealed no production of 1,4-cyclohexanediol.

EXAMPLE 2

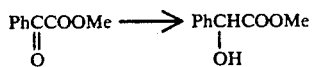

In 1.0 ml of DME, 1.0 mmol of methylbenzoyl formate and 0.01 mmol of tetraethylammonium μ-hydride-bis(pentacarbonylchromium (O)) were heated at 100° C. at a hydrogen pressure of 50 atm for 60 hours while being stirred. GLC analysis of the reaction mixture revealed that methyl 1-hydroxy-1-phenylacetate was produced in a yield of 91%.

EXAMPLE 3

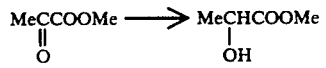

In 1.0 ml of DME, 1.0 mmol of methyl pyruvate and 0.01 mmol of tetraethylammonium μ-hydride-bis(pentacarbonylchromium (O)) were heated at 100° C. at a hydrogen pressure of 50 atm for 60 hours with stirring. GLC analysis of the reaction mixture revealed that methyl butyrate was produced in a yield of 82%.

EXAMPLE 4

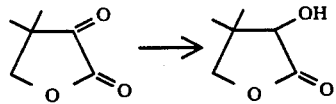

In 1.0 ml of DME, 1.0 mmol of ketopantoyllactone and 0.02 mmol of benzenechromium tricarbonyl were heated at 100° C. at a hydrogen pressure of 50 atm for 13 hours with stirring. GLC analysis of the reaction mixture revealed that pantolactone was produced in a yield of 52%.

COMPARATIVE EXAMPLE 2

In 1.0 ml of DME, 1.0 mmol of ketopantoyllactone and 0.02 mmol of benzenechromium tricarbonyl were heated at 100° C. at a hydrogen pressure of 50 atm for 13 hours while being stirred. GLC analysis of the reaction mixture revealed no production of pantolactone.

EXAMPLE 5

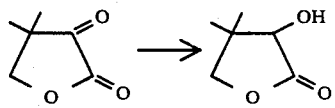

In 1.0 ml of DME, 1.0 mmol of ketopantoyllactone and 0.01 mmol of tetraethylammonium µ-hydride-bis(-pentacarbonylchromium(O)) were heated at 100° C. at a hydrogen pressure of 50 atm for 60 hours while being stirred. GLC analysis of the reaction mixture revealed that pantolactone was produced in a yield of 99%.

EXAMPLE 6

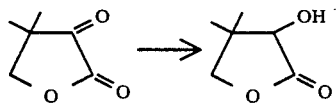

In 1.0 ml of DME were heated 1.0 mmol of ketopantoyllactone, 0.01 mmol of tetraethylammonium µ-hydride-bis-(pentacarbonylchromium(O)), and 0.01 mmol of (−)-2,3-O-isopropylidene-2,3-dihydroxy-1,4-bis(diphenylphosphino)butane [(−)-DIOP)] at 100° C. at a hydrogen pressure of 50 atm for 60 hours while being stirred. GLC analysis of the reaction mixture revealed that pantolactone was produced in a yield of 99%.

EXAMPLE 7

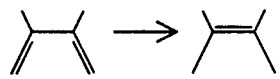

In 1.0 ml of DME were heated 1.0 mmol of 2,3-dimethylbutadiene and 0.01 mmol of tetraethylammonium µ-hydride-bis(pentacarbonylchromium(O)), and at 100° C. at a hydrogen pressure of 50 atm for 60 hours while being stirred. GLC analysis of the reaction mixture revealed that 2,3-dimethyl-2-butene was produced in a yield of 60%.

EXAMPLE 8

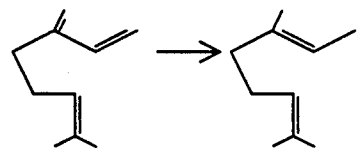

In 1.0 ml of DME were heated 1.0 mmol of myrcene and 0.01 mmol of tetraethylammonium µ-hydride-bis(-pentacarbonylchromium(O)), and at 100° C. at a hydrogen pressure of 50 atm for 60 hours while being stirred. GLC analysis of the reaction mixture revealed that 2,6-dimethyl-2,6-octadiene was produced in a yield of 100%.

COMPARATIVE EXAMPLE 3

In 1.0 ml of DME were heated 1.0 mmol of myrcene and 0.01 mmol of benzenechromium tricarbonyl at 100° C. at a hydrogen pressure of 50 atm for 60 hours with stirring. GLC analysis of the reaction mixture revealed no production of 2,6-dimethyl-2,6-octadiene.

EXAMPLE 9

In 1.0 ml of DME were heated 1.0 mmol of styrene and 0.01 mmol of tetraethylammonium µ-hydride-bis(-pentacarbonylchromium(O)) at 100° C. and at a hydrogen pressure of 50 atm for 84 hours with stirring. GLC analysis of the reaction mixture revealed that ethylbenzene was produced in a yield of 80%.

EXAMPLE 10

In 1.0 ml of DME were heated 1.0 mmol of styrene and 0.01 mmol of tetraethylammonium µ-hydride-bis(-pentacarbonylchromium(O)) at 100° C. and at a hydrogen pressure of 50 atm for 13 hours with stirring. GLC analysis of the reaction mixture revealed that ethylbenzene was produced in a yield 29%.

EXAMPLE 11

In 1.0 ml of DME were heated 1.0 mmol of styrene and 0.01 mmol of tetrabutylammonium µ-hydride-bis(-pentacarbonylchromium(O)) at 100° C. and at a hydrogen pressure of 50 atm for 13 hours while being stirred. GLC analysis of the reaction mixture revealed that ethylbenzene was produced in a yield of 44%.

EXAMPLE 12

In 1.0 ml of DME were heated 1.0 mmol of styrene and 0.01 mmol of bis(triphenylposphine)iminium µ-hydride-bis(pentacarbonylchromium(O)) at 100° C. and at a hydrogen pressure of 50 atm for 13 hours while being stirred. GLC analysis of the reaction mixture revealed that ethylbenzene was produced in a yield of 42%.

COMPARATIVE EXAMPLE 4

In 1.0 ml of DME were heated 1.0 mmol of styrene and 0.01 mmol of benzenechromium tricarbonyl at 100° C. and at a hydrogen pressure of 50 atm for 13 hours while being stirred. GLC analysis of the reaction mixture revealed no production of ethylbenzene.

EXAMPLE 13

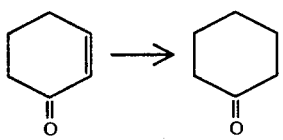

In 1.0 ml of DME were heated 1.0 mmol of 2-cyclohexene-1-one and 0.01 mmol of tetraethylammonium μ-hydride-bis(pentacarbonylchromium(O)) at 100° C. and at a hydrogen pressure of 50 atm for 13 hours with stirring. GLC analysis of the reaction mixture revealed that cyclohexanone was produced in a yield of 75%.

EXAMPLE 14

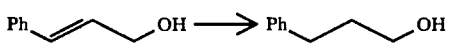

In 1.0 ml of DME were heated 1.0 mmol of cinnamyl alcohol and 0.01 mmol of tetraethylammonium μ-hydride-bis(pentacarbonylchromium(O)) at 100° C. and at a hydrogen pressure of 50 atm for 60 hours while being stirred. GLC analysis of the reaction mixture revealed that 3-phenylpropanol was produced in a yield of 100%.

EXAMPLE 15

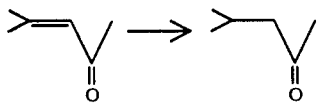

In 1.0 ml of DME were heated 1.0 mmol of 4-methyl-3-penten-2-one and 0.01 mmol of tetraethylammonium μ-hydride-bis(pentacarbonylchromium(O)) at 100° C. and at a hydrogen pressure of 50 atm for 13 hours with stirring. GLC analysis of the reaction mixture revealed that 4-methyl-2-pentanone was produced in a yield of 60%.

EXAMPLE 16

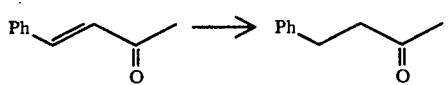

In 1.0 ml of DME were heated 1.0 mmol of benzalacetone and 0.01 mmol of tetraethylammonium μ-hydride-bis(pentacarbonylchromium(O)) at 100° C. and at a hydrogen pressure of 50 atm for 13 hours with stirring. GLC analysis of the reaction mixture revealed that 4-phenyl-2-butanone was produced in a yield of 82%.

EXAMPLE 17

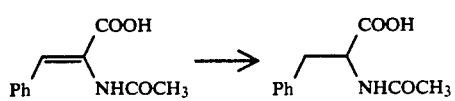

In 1.0 ml of DME were heated 1.0 mmol of β-phenyl-α-acetylaminoacrylic acid and 0.01 mmol of tetraethylammonium μ-hydride-bis(pentacarbonylchromium(O)) at 100° C. and at a hydrogen pressure of 50 atm for 60 hours with stirring. The reaction mixture was treated with an ion exchange resin and then analyzed by $^1$H-NMR. As a result, it was found that N-acetylphenylalanine was produced in a yield of 50%.

EXAMPLE 18

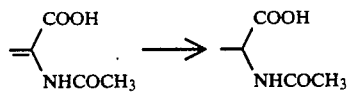

In 1.0 ml of DME were heated 1.0 mmol of α-acetylaminoarylic acid and 0.01 mmol of tetraethylammonium μ-hydride-bis(pentacarbonylchromium(O)) at 100° C. and at a hydrogen pressure of 50 atm for 60 hours with stirring. The reaction mixture was treated with an ion exchange resin and then analyzed by $^1$H-NMR. As a result, it was found that N-acetylalanine was produced in a yield of 100%.

EXAMPLE 19

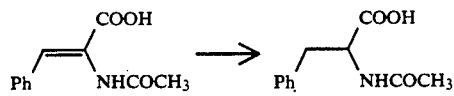

In 1.0 ml of DME were heated 1.0 mmol of β-phenyl-α-acetylaminoacrylic acid, 0.01 mmol of tetraethylammonium μ-hydride-bis(pentacarbonylchromium(O)), and 0.01 mmol of (−)-2,3-O-isopropylidene-2,3-dihydroxy-1,4-bis(diphenylphosphino)butane [(−)-DIPOP] at 100° C. and at a hydrogen pressure of 50 atm for 72 hours with stirring. The reaction mixture was treated with an ion exchange resin and then analyzed by $^1$H-NMR. As a result, it was found that N-acetylphenylalanine was produced in a yield of 57%.

Optical purity: 13.0% ee

EXAMPLE 20

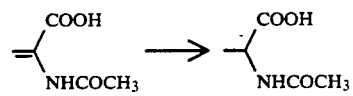

In 1.0 ml of DME were heated 1.0 mmol of α-acetylaminoacrylic acid, 0.01 mmol of tetraethylammonium μ-hydride-bis(pentacarbonylchromium(O)), and 1.0 mmol of (−)-2,3-O-isopropylidene-2,3-dihydroxy-1,4-bis(diphenylphosphino)butane [(−)-DIOP] at 100° C. and at a hydrogen pressure of 50 atm for 72 hours while being stirred. The reaction mixture was treated with an ion exchange resin and then analyzed by $^1$H-NMR. As a result, it was found that N-acetylphenylalanine was produced in a yield of 96%.

Optical purity: 6.8% ee

EXAMPLE 21

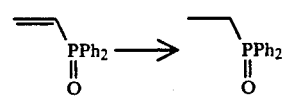

In 1.0 ml of DME were heated 1.0 mmol of vinyldiphenylphosphine oxide and 0.01 mmol of tetraethylammonium μ-hydride-bis(pentacarbonylchromium(O)) at 100° C. and at a hydrogen pressure of 50 atm for 13 hours with stirring. GLC analysis of the reaction mixture revealed that ethyldiphenylphosphine oxide was produced in a yield of 100%.

EXAMPLE 22

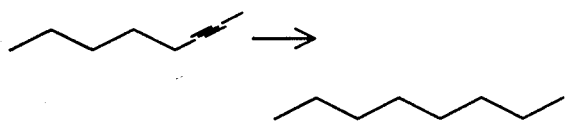

In 1.0 ml of DME were heated 1.0 mmol of 2-octyne and 0.01 mmol of tetraethylammonium μ-hydride-bis(-pentacarbonylchromium(O)) at 100° C. and at a hydrogen pressure of 50 atm for 48 hours while being stirred. GLC analysis of the reaction mixture revealed that octane was produced in a yield of 100%.

EXAMPLE 23

In 1.0 ml of DME were heated 1.0 mmol of 1-phenyl-1-propyne and 0.01 mmol of tetraethylammonium μ-hydride-bis(pentacarbonylchromium(O)) at 100° C. and at a hydrogen pressure of 50 atm for 18 hours with stirring. GLC analysis of the reaction mixture revealed that propylbenzene and β-methylstyrene were produced in a yield of 79% and 19%, respectively.

COMPARATIVE EXAMPLE 5

In 1.0 ml of DME were heated 1.0 mmol of 1-phenyl-1-propyne and 0.02 mmol of benzenechromium tricarbonyl at 100° C. and at a hydrogen pressure of 50 atm for 60 hours with stirring. GLC analysis of the reaction mixture revealed that β-methylstyrene was produced in a yield of 27%.

EXAMPLE 24

In 1.0 ml of DME were heated 1.0 mmol of 1-phenyl-1-propyne and 0.01 mmol of tetraethylammonium μ-hydride-bis(pentacarbonylchromium(O)) at 100° C. and at a hydrogen pressure of 50 atm for 13 hours with stirring. GLC analysis of the reaction mixture revealed that propylbenzene and β-methylstyrene were produced in a yield of 46% and 10%, respectively.

EXAMPLE 25

In 1.0 ml of DME were heated 1.0 mmol of 1-phenyl-1-propyne and 0.01 mmol of tetraethylammonium μ-hydride-bis(pentacarbonylchromium(O)) at 100° C. and at a hydrogen pressure of 50 atm for 13 hours with stirring. GLC analysis of the reaction mixture revealed that propylbenzene and β-methylstyrene were produced in a yield of 82% and 11%, respectively.

EXAMPLE 26

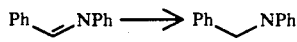

In 1.0 ml of DME were heated 1.0 mmol of benzylideneaniline and 0.01 mmol of tetraethylammonium μ-hydride-bis(pentacarbonylchromium(O)) at 100° C. and at a hydrogen pressure of 50 atm for 60 hours with stirring. GLC analysis of the reaction mixture revealed that phenylbenzylamine was produced in a yield of 58%.

EXAMPLE 27

In 1.0 ml of DME were heated 1.0 mmol of benzonitrile and 0.05 mmol of tetraethylammonium μ-hydridebis(pentacarbonylchromium(O)) at 120° C. and at a hydrogen pressure of 50 atm for 60 hours while being stirred. GLC analysis of the reaction mixture revealed that benzylamine was produced in a yield of 10%.

EXAMPLE 28

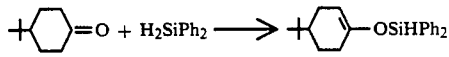

4-t-Butylcyclohexanone (154.2 mg, 1.0 mmol), 184.3 mg (1.0 mmol) of diphenylsilane, and 7.8 mg (0.01 mmol) of tetraethylammonium μ-hydridebis(pentacarbonyltungsten) were heated in a sealed tube at 100° C. for 24 hours while being stirred. GLC analysis of the reaction mixture revealed that 4-t-butyl-1-diphenylsiloxy-1-cyclohexene in a yield of 98%. 4-t-butyl-1-diphenylsiloxy-1-cyclohexene:
Boiling point: >250° C./1 mmHg
$^1$H-NMR (CDCl$_3$): δ 0.84 (s, 9H), 1.1–2.5 (m, 7H), 4.96 (t, 1H), 5.54 (s, 1H), 7.3–7.8 (m, 10H)

EXAMPLES 29 TO 34

In the same manner as in Example 50, a reaction was conducted by using various hydrosilanes and catalysts. The kind of the hydrosilane and catalyst used, reaction time, solvent, and yield in each reaction are shown in Table 1 below.

TABLE 1

| Example No. | Hydrosilane R$_2$SiH$_2$ | Catalyst A | M | Reaction Time (hr) | solvent | Yield (%) |
|---|---|---|---|---|---|---|
| 29 | Ph | Et$_4$ | Cr | 16 | — | 84.2 |
| 30 | Ph | Et$_4$ | Mo | 16 | DME | 47.6 |
| 31 | Ph | Et$_4$ | W | 24 | DME | 96.1 |
| 32 | Ph | Et$_4$ | Cr | 16 | DME | 89.0 |
| 33 | Et | Et$_4$ | Cr | 16 | DME | 58.9 |
| 34 | Ph | (Ph$_3$P)$_2$N | Cr | 16 | DME | 77.2 |

COMPARATIVE EXAMPLE 6

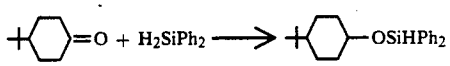

4-t-Butylcyclohexanone (154.2 mg, 1.0 mmol), 184.3 mg (1.0 mmol) of diphenylsilane, 9.3 mg (0.01 mmol) of tris(triphenylphosphine)rhodium(I) chloride, and 1.0 ml of dimethoxyethane (DME) were heated in a sealed tube at 100° C. for 24 hours while being stirred. GLC analysis of the reaction mixture revealed that 4-t-butyl-1-diphenylsiloxycyclohexane in a yield of 98%.

COMPARATIVE EXAMPLE 7

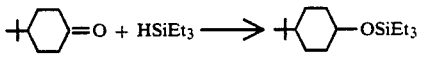

A reaction was carried out in the same manner as in Comparative Example 9, except for using triethylsilane. There was obtained 4-t-butyl-1-triethylsiloxycyclohexane in a yield of 96%.

COMPARATIVE EXAMPLE 8

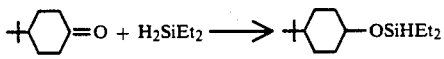

A reaction was carried out in the same manner as in Comparative Example 9, except for using diethylsilane. There was obtained 4-t-butyl-1-diphenylsiloxycyclohexane in a yield of 96%.

EXAMPLE 35

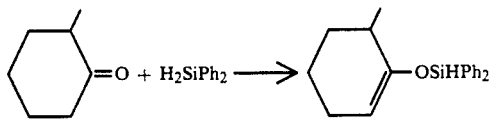

A mixture of 112.2 mg (1.0 mmol) of 2-methylcyclohexanone, 184.3 mg (1.0 mmol) of diphenylsilane, and 7.8 mg (0.01 mmol) of tetraethylammonium $\mu$-hydridebis(pentacarbonyltungsten) was heated in a sealed tube at 100° C. for 24 hours while being stirred. GLC analysis of the reaction mixture revealed that 2-methyl-1-diphenylsiloxy-6-cyclohexene was produced in a yield of 82%.

Boiling point: >250° C./1 mmHg
$^1$H-NMR (CDCl$_3$): $\delta$ 1.1–2.0 (m, 7H), 1.11 (d, 3H), 4.89 (t, 1H), 5.56 (s, 1H), 7.3–7.7 (m, 10H)

EXAMPLE 36

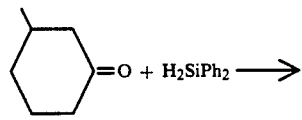

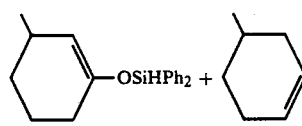

A mixture of 112.2 mg (1.0 mmol) of 3-methylcyclohexanone, 184.3 mg (1.0 mmol) of diphenylsilane, and 7.9 mg (0.01 mmol) of tetraethylammonium $\mu$-hydridebis(pentacarbonyltungsten) was heated in a closed tube at 100° C. for 24 hours while being stirred. GLC analysis of the reaction mixture revealed that 3-methyl-1-diphenylsiloxy-1-cyclohexene an 4-methyl-2-diphenylsiloxy-1-cyclohexene were produced in a yield of 35% and 40%, respectively. 3-Methyl-1-diphenylsiloxy-1-cyclohexene:

Boiling point: >250° C./1 mmHg
$^1$H-NMR (CDCl$_3$): $\delta$0.7–2.3 (m, 7H), 0.84 (d, 3H), 4.86 (d, 1H), 5.56 (s, 1H), 7.2–7.8 (m, 10H)

4-Methyl-2-diphenylsiloxy-1-cyclohexene:
Boiling point: >250° C./1 mmHg
$^1$H-NMR (CDCl$_3$): $\delta$0.7–2.3 (m, 7H), 0.88 (d, 3H), 4.96 (t, 1H), 5.55 (s, 1H), 7.2–7.8 (m, 10H)

EXAMPLE 37

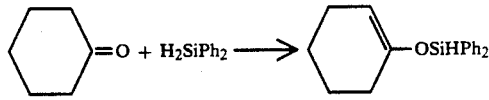

A mixture of 98.2 mg (1.0 mmol) of cyclohexanone, 184.3 mg (1.0 mmol) of diphenylsilane, 7.8 mg (0.01 mmol) of tetraethylammonium $\mu$-hydridebis(pentacarbonyltungsten), and 1.0 ml of dimethoxyethane (DME) was heated in a sealed tube at 100° C. for 24 hours while being stirred. GLC analysis of the reaction mixture revealed that 1-diphenylsiloxy-1-cyclohexene was produced in a yield of 84%. 1-Diphenylsiloxy-1-cyclohexene:

Boiling point: >250° C./1 mmHg
$^1$H-NMR (CDCl$_3$): $\delta$ 1.0–2.6 (m, 8H), 5.0 (t, 1H), 5.56 (s, 1H), 7.1–7.9 (m, 10H)

EXAMPLE 38

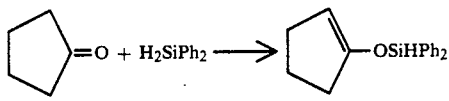

A mixture of 84.1 mg (1.0 mmol) of cyclopentanone, 184.3 mg (1.0 mmol) of diphenylsilane, 7.8 mg (0.01 mmol) of tetraethylammonium $\mu$-hydridebis(pentacarbonyltungsten), and 1.0 ml of dimethoxyethane (DME) was heated in a sealed tube at 100° C. for 24 hours while being stirred. GLC analysis of the reaction mixture revealed that 1-diphenylsiloxy-1-cyclohexene was produced in a yield of 70%. 1-Diphenylsiloxy-1-cyclohexene:

$^1$H-NMR (CDCl$_3$): $\delta$ 1.1–1.6 (m, 6H), 4.73 (t, 1H), 5.58 (s, 1H), 7.2–7.8 (m, 10H)

EXAMPLE 39

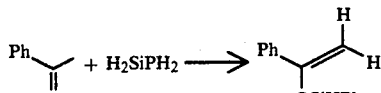

A mixture of 120.2 mg (1.0 mmol) of acetophenone, 184.3 mg (1.0 mmol) of diphenylsilane, 7.8 mg (0.01 mmol) of tetraethylammonium $\mu$-hydridebis(pentacarbonyltungsten), and 1.0 ml of dimethoxyethane (DME) was heated in a sealed tube at 100° C. for 24 hours while being stirred. GLC analysis of the reaction mixture revealed that $\alpha$-(diphenylsiloxy)styrene was produced in a yield of 90%.

¹H-NMR (CDCl₃): δ 4.52, 4.98 (dd, 2H), 5.72 (s, 1H), 7.1-8.1 (m, 15H)

EXAMPLE 40

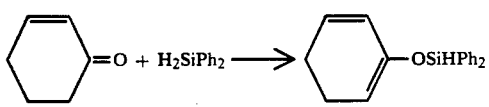

A mixture of 96.1 mg (1.0 mmol) of 2-cyclohexen-1-one, 184.3 mg (1.0 mmol) of diphenylsilane, 7.8 mg (0.01 mmol) of tetraethylammonium μ-hydridebis(pentacarbonyltungsten), and 1.0 ml of dimethoxyethane (DME) was heated in a sealed tube at 100° C. for 24 hours while being stirred. GLC analysis of the reaction mixture revealed that 2-diphenylsiloxy-1,3-cyclohexadiene was produced in a yield of 32%.

EXAMPLE 41

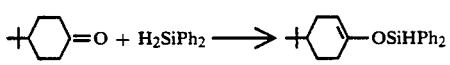

Sodium μ-hydridebis(pentacarbonylchromium) prepared from chromium hexacarbonyl and sodium borohydride in situ was used as a catalyst. That is, 154.2 mg (1.0 mmol) of 4-t-butylcyclohexanone, 184.3 mg (1.0 mmol) of diphenylsilane, 4.4 mg (0.02 mmol) of chromium hexacarbonyl, 4 mg (0.10 mmol) of sodium borohydride, and 1.0 ml of dimethoxyethane (DME) were heated in a sealed tube at 100° C. for 16 hours while being stirred. GLC analysis of the reaction mixture revealed that 4-t-butyl-1-diphenylhydrosiloxycyclohexene in a yield of 67%.

EXAMPLE 42

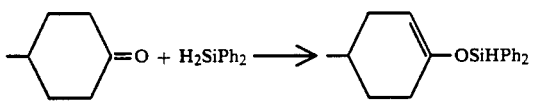

Tetraethylammonium μ-hydridebis(pentacarbonyltungsten) prepared from tungsten hexacarbonyl and tetraethylammonium borohydride in situ was used as a catalyst. A mixture of 154.2 mg (1.0 mmol) of 4-t-butylcyclohexanone, 184.3 mg (1.0 mmol) of diphenylsilane, 7.0 mg (0.02 mmol) of tungsten hexacarbonyl, 21 mg (0.10 mmol) of tetraethylammonium borohydride, and 1.0 ml of dimethoxyethane (DME) were heated in a sealed tube at 100° C. for 24 hours while being stirred. GLC analysis of the reaction mixture revealed that 4-t-butyl-1-diphenylhydrosiloxycyclohexene was produced in a yield of 69%.

EXAMPLE 43

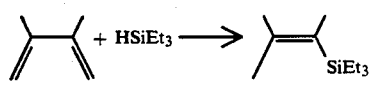

A mixture of 0.113 ml (1.0 mmol) of 2,3-dimethylbutadiene, 0.912 ml (1.2 mmol) of triethylsilane, and 5.2 mg (0.01 mmol) of tetraethylammonium μ-hydridebis(pentacarbonylchromium) was heated in a sealed tube at 100° C. for 60 hours while being stirred. GLC analysis of the reaction mixture revealed that 2,3-dimethyl-2-butenyltriethylsilane was produced in a yield of 99%.

¹H-NMR (CDCl₃): δ 0.53 (q, 6H), 0.94 (t, 9H), 1.53 (s, 2H), 1.61 (s, 3H), 1.63 (s, 6H)

EXAMPLE 44

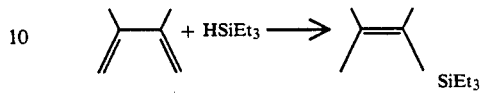

A mixture of 0.136 ml (1.2 mmol) of 2,3-dimethylbutadiene, 0.160 ml (1.0 mmol) of triethylsilane, and 6.0 mg (0.01 mmol) of tetraethylammonium μ-hydridebis(pentacarbonylmolybdenum) was heated in a sealed tube at 100° C. for 24 hours while being stirred. GLC analysis of the reaction mixture revealed that 2,3-dimethyl-2-butenyltriethylsilane was produced in a yield of 94%.

EXAMPLE 45

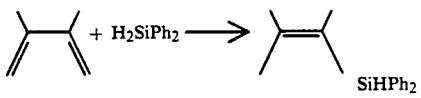

A mixture of 0.113 ml (1.0 mmol) of 2,3-dimethylbutadiene, 0.223 ml (1.2 mmol) of dephenylsilane, and 5.2 mg (0.01 mmol) of tetraethylammonium μ-hydridebis(pentacarbonylchromium) was heated in a sealed tube at 100° C. for 60 hours while being stirred. GLC analysis of the reaction mixture revealed that 2,3-dimethyl-2-butenyltriethylsilane was produced in a yield of 57%.

¹H-NMR (CDCl₃): δ 1.44 (s, 3H), 1.59 (s, 6H), 2.09 (d, 2H), 4.87 (m, 1H), 7.31-7.84 (s, 10H)

EXAMPLE 46

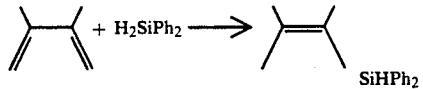

A mixture of 0.136 ml (1.2 mmol) of 2,3-dimethylbutadiene, 0.186 ml (1.0 mmol) of dephenylsilane, and 6.0 mg (0.01 mmol) of tetraethylammonium μ-hydridebis(pentacarbonylmolybdenum) was heated in a sealed tube at 100° C. for 24 hours. GLC analysis of the reaction mixture revealed that 2,3-dimethyl-2-butenyldiphenylsilane in a yield of 75%.

EXAMPLE 47

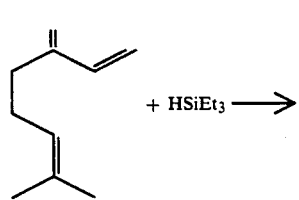

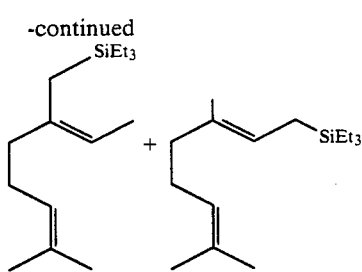

A mixture of 0.170 ml (1.0 mmol) of myrcene, 0.192 ml (1.2 mmol) of triethylsilane, and 5.2 mg (0.01 mmol) of tetraethylammonium μ-hydridebis(pentacarbonylchromium) was heated in a sealed tube at 100° C. for 60 hours while being stirred. GLC analysis of the reaction mixture revealed that 6-(triethylsilyl)methyl-2-methyl-2,6-octadiene and 8-triethylsilyl-2,6-dimethyl-2,6-octadiene were produced at a ratio of about 7:3 in a yield of 91%. 6-(Triethylsilyl)methyl-2-methyl-2,6-octadiene:

$^1$H-NMR (CDCl$_3$): δ 0.55 (q, 6H), 0.95 (t, 9H), 1.55 (d, J=6.6 Hz, 2H), 1.55 (s, 3H), 1.61 (s, 3H), 1.69 (d, J=1.4 Hz, 3H), 1.94 (t, J=7.6 Hz, 2H), 2.08 (d, t, J=6.9, 7.6 Hz, 2H), 5.08 (q, J=6.6 Hz), 1H), 5.11 (t, q, J=6.9, 1.4 Hz, 1H)

8-Triethylsilyl-2,6-dimethyl-2,6-octadiene:
$^1$H-NMR (CDCl$_3$): δ 0.52 (q, 6H), 0.94 (t, 9H), 1.42 (d, J=8.5 Hz, 2H), 1.52 (s, 3H), 1.57 (s, 3H), 1.68 (d, J=1.1 Hz, 3H), 2.00 (m, 2H), 2.08 (m, 2H), 5.08 (m, 1H), 5.17 (m, 1H)

EXAMPLE 48

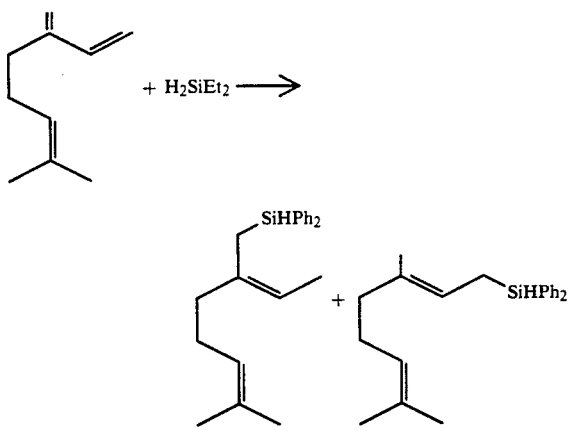

A mixture of 0.170 ml (1.0 mmol) of myrcene, 0.186 ml (1.2 mmol) of diphenylsilane, and 6.0 mg (0.01 mmol) of tetraethylammonium μ-hydridebis(pentacarbonylmolybdenum) was heated in a sealed tube at 100° C. for 24 hours while being stirred. GLC analysis of the reaction mixture revealed that 6-(diphenylsilyl)methyl-2-methyl-2,6-octadiene and 8-diphenylsilyl-2,6-dimethyl-2,6-octadiene were produced at a ratio of about 75:25 in a total yield of 95%. 6-(Diphenylsilyl)methyl-2-methyl-2,6-octadiene:

$^1$H-NMR (CDCl$_3$): δ 1.38 (d, J=6.7 Hz, 3H), 1.54 (s, 3H), 1.65 (s, 3H), 1.90 (t, J=7.1 Hz, 2H), 2.03 (t, d, J=7.1, 7.0 Hz, 2H), 2.10 (d, J=4.0 Hz, 2H), 4.89 (d, J=4.0 Hz, 1H), 5.01 (t, m, J=7.0 Hz, 1H), 5.14 (q, J=6.7 Hz) 7.34–7.57 (m, 10H)

8-Diphenylsilyl-2,6-Dimethyl-2,6-Octadiene:

$^1$H-NMR (CDCl$_3$): δ 1.46 (s, 3H), 1.54 (s, 3H), 1.65 (s, 3H), 1.89–2.09 (m, 5H),
4.82 (t, J=3.5 Hz, 1H), 5.03 (t, m, J=5.9 Hz, 1H), 5.24 (t, J=8.2 Hz), 7.34–7.57 (m, 10H)

EXAMPLE 49

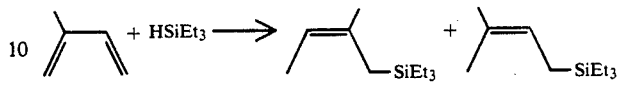

A mixture of 0.120 ml (1.2 mmol) of 2-methylbutadiene, 0.160 ml (1.0 mmol) of triethylsilane, and 6.0 mg (0.01 mmol) of tetraethylammonium μ-hydridebis(pentacarbonylmolybdenum) was heated in a sealed tube at 100° C. for 24 hours while being stirred. GLC analysis of the reaction mixture revealed that 2-methyl-2-butenyldiphenylsilane and 3-methyl-2-butenyltriethylsilane were produced as a 8:1 mixture in a total yield of 71%.

2-Methyl-2-butenyltriethylsilane:
$^1$H-NMR (CDCl$_3$): δ 0.55 (q, 6H), 0.95 (t, 9H), 1.51 (q, J=1.4 Hz, 2H), 1.52 (d, J=6.5 Hz, 3H), 1.68 (t, J=1.4 Hz, 3H), 5.06 (q, J=6.5 Hz, 1H), 3-Methyl-2-butenyltriethylsilane:
$^1$H-NMR (CDCl$_3$): δ 0.52 (q, 6H), 0.93 (t, 9H), 1.52 (d, J=5.6 Hz, 2H), 1.57 (s, 3H), 1.68 (s, 3H), 5.14 (t, J=5.6 Hz, 1H)

EXAMPLE 50

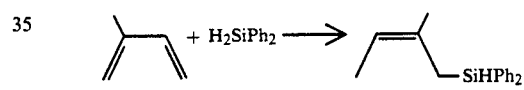

A mixture of 0.120 ml (1.2 mmol) of 2-methylbutadiene, 0.186 ml (1.0 mmol) of diphenylsilane, and 6.0 mg (0.01 mmol) of tetraethylammonium μ-hydridebis(pentacarbonylmolybdenum) was heated in a sealed tube at 100° C. for 24 hours while being stirred. GLC analysis of the reaction mixture revealed that 2-methyl-2-butenyldiphenylsilane was produced in a yield of 97%.

$^1$H-NMR (CDCl$_3$): δ 1.37 (m, 2H), 1.61 (m, 3H), 2.18 (m, 3H), 4.88 (t, J=4.0 Hz, 1H), 5.09 (q, J=6.7 Hz, 1H), 7.34–7.65 (m, 10H)

EXAMPLE 51

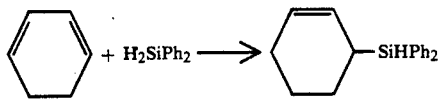

A mixture of 0.114 ml (1.2 mmol) of 1,3-cyclohexadiene, 0.186 ml (1.0 mmol) of diphenylsilane, and 6.0 mg (0.01 mmol) of tetraethylammonium μ-hydridebis(pentacarbonylmolybdenum) was heated in a sealed tube at 100° C. for 24 hours while being stirred. GLC analysis of the reaction mixture revealed that 3-diphenylsilyl-1-cyclohexene was produced in a yield of 99%.

$^1$H-NMR (CDCl$_3$): δ 1.62 (m, 1H), 1.70 (m, 2H), 1.89 (m, 2H), 1.97 (m, 2H), 4.75 (d, J=4.0 Hz, 1H), 7.63 (m, 2H), 7.38–7.66 (m, 10H)

EXAMPLE 52

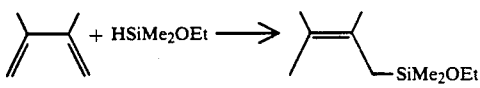

A mixture of 0.136 ml (1.2 mmol) of 2,3-dimethylbutadiene, 0.130 ml (1.0 mmol) of dimethylethoxysilane, and 6.0 mg (0.01 mmol) of tetraethylammonium μ-hydridebis(pentacarbonylmolybdenum) was heated in a sealed tube at 100° C. for 21.5 hours while being stirred. GLC analysis of the reaction mixture revealed that 2,3-dimethyl-2-butenyldimethylethoxysilane in a yield of 55%.

$^1$H-NMR (CDCl$_3$): δ 0.10 (s, 6H), 1.18 (t, J=7.2 Hz, 3H), 1.48 (s, 2H), 1.63 (s, 2H), 1.65 (m, 6H), 3.67 (q, J=7.2 Hz, 2H)

COMPARATIVE EXAMPLE 9

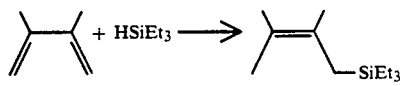

A mixture of 0.136 ml (1.2 mmol) of 2,3-dimethylbutadiene, 0.160 ml (1.0 mmol) of triethylsilane, and 9.9 mg (0.01 mmol) of tris(triphenylphosphine)rhodium chloride was heated in a sealed tube at 100° C. for 24 hours. GLC analysis of the reaction mixture revealed that 2,3-dimethyl-2-butenyldiphenylsilane in a yield of 55%.

$^1$H-NMR (CDCl$_3$): δ 1.40 (t, —CH$_3$, 12H), 3.47 (q, —CH$_2$—, 8H),

EXAMPLE 53

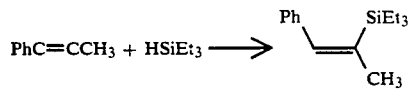

A mixture of 0.125 ml (1.0 mmol) of 1-phenylpropyne, 0.192 ml (1.2 mmol) of triethylsilane, and 5.2 mg (0.01 mmol) of tetraethylammonium μ-hydridebis(pentacarbonylchromium) was heated in a sealed tube at 100° C. for 16 hours while being stirred. GLC analysis of the reaction mixture revealed that (Z)-β-triethylsilyl-β-methylstyrene and (Z)-α-triethylsilyl-β-methylstyrene were produced in a yield of 95% and 2%, respectively, with no production of other isomers.

(Z)-β-Triethylsilyl-β-methylstyrene
$^1$H-NMR (CDCl$_3$): δ 0.64 (q, 6H), 0.91 (t, 9H), 1.90 (d, J=7 Hz, 3H), 6.22 (q, J=7 Hz, 1H), 6.97-7.33 (m, 5H)

(Z)-α-Triethylsilyl-β-methylstyrene
$^1$H-NMR (CDCl$_3$): δ 0.43 (q, 6H), 0.83 (t, 9H), 1.95 (d, J=2 Hz, 3H), 7.15-7.28 (m, 6H)

COMPARATIVE EXAMPLE 10

A mixture of 0.125 ml (1.0 mmol) of 1-phenylpropyne, 0.192 ml (1.2 mmol) of triethylsilane, and 9.9 mg (0.01 mmol) of chlorodium tris(triphenylphosphine) rhodium chloride was heated in a sealed tube at 100° C. for 16 hours while being stirred. GLC analysis of the reaction mixture revealed that (Z)-β-triethylsilyl-β-methylstyrene, (E)-β-triethylsilyl-β-methylstyrene, (Z)-α-triethylsilyl-β-methylstyrene, and (E)-α-triethylsilyl-β-methylstyrene were produced in a yield of 4%, 33%, 7%, and 56%, respectively.

(E)-β-Triethylsilyl-β-methylstyrene:
$^1$H-NMR (CDCl$_3$): δ 0.68 (q, 6H), 0.98 (t, 9H), 1.93 (d, J=2 Hz, 3H), 6.71 (d, J=2 Hz), 7.17-7.35 (m, 5H)

(E)-α-Triethylsilyl-β-methylstyrene:
$^1$H-NMR (CDCl$_3$): δ 0.55 (q, 6H), 0.90 (t, 9H), 1.56 (d, J=6.5 Hz, 3H), 6.06 (q, J=6.5 Hz, 1H), 6.91-7.30 (m, 5H)

EXAMPLE 54

A mixture of 0.125 ml (1.0 mmol) of 1-phenylpropyne, 0.192 ml (1.2 mmol) of triethylsilane, and 8.3 mg (0.01 mmol) of bis(triphenylphosphine)iminium μ-hydridebis(pentacarbonylchromium) was heated in a sealed tube at 100° C. for 16 hours while being stirred. GLC analysis of the reaction mixture revealed that (Z)-β-triethylsilyl-β-methylstyrene and (Z)-α-triethylsilyl-β-methylstyrene were produced in a yield of 86% and 4%, respectively.

EXAMPLE 55

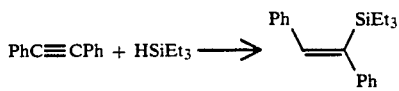

A mixture of 0.178 ml (1.0 mmol) of diphenylacetylene, 0.192 ml (1.2 mmol) of triethylsilane, and 5.2 mg (0.01 mmol) of tetraethylammonium μ-hydridebis(pentacarbonylchromium) was heated in a sealed tube at 100° C. for 16 hours while being stirred. GLC analysis of the reaction mixture revealed that α,β-diphenylvinyltriethylsilane in a yield of 50% at an E/Z ratio of 2/98.

(E)-α,β-Diphenylvinyltriethylsilane
$^1$H-NMR (CDCl$_3$): δ 0.48 (q, 6H), 0.80 (t, 9H), 7.17-7.36 (m, 11H)

(Z)-α,β-Diphenylvinyltriethylsilane
$^1$H-NMR (CDCl$_3$): δ 0.70 (q, 6H), 0.99 (t, 9H), 6.90 (s, 1H), 7.00-7.12 (m, 10H)

COMPARATIVE EXAMPLE 11

A mixture of 0.178 ml (1.0 mmol) of diphenylacetylene, 0.192 ml (1.2 mmol) of triethylsilane, and 9.9 mg (0.01 mmol) of chlorodium tris(triphenylphosphine) was heated in a sealed tube at 100° C. for 16 hours while being stirred. GLC analysis of the reaction mixture revealed that α,β-diphenylvinyltriethylsilane was produced in a yield of 21% at an E/Z ratio of 82/18.

EXAMPLE 56

A mixture of 0.178 ml (1.0 mmol) of diphenylacetylene, 0.192 ml (1.2 mmol) of triethylsilane, and 6.0 mg (0.01 mmol) of tetraethylammonium μ-hydridebis(pentacarbonylmolybdenum) was heated in a sealed tube at 100° C. for 60 hours while being stirred. GLC analysis of the reaction mixture revealed that α,β-diphenylvinyltriethylsilane was produced in a yield of 62% at an E/Z ratio of 9/91.

EXAMPLE 57

A mixture of 0.178 ml (1.0 mmol) of diphenylacetylene, 0.192 ml (1.2 mmol) of triethylsilane, and 7.8 mg (0.01 mmol) of tetraethylammonium μ-hydridebis(pentacarbonyltungsten) was heated in a sealed tube at 100° C. for 60 hours while being stirred. GLC analysis of the reaction mixture revealed that α,β-diphenylvinyltriethylsilane was produced in a yield of 52% at an E/Z ratio of 3/97.

EXAMPLE 58

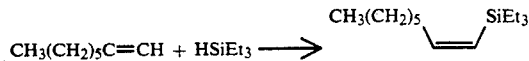

A mixture of 0.148 ml (1.0 mmol) of 1-octyne, 0.192 ml (1.2 mmol) of triethylsilane, and 5.2 mg (0.01 mmol) of tetraethylammonium μ-hydridebis(pentacarbonylchromium) was heated in a selaed tube at 100° C. for 60 hours while being stirred. GLC analysis of the reaction mixture revealed that (Z)-1-octenyltriethylsilane was produced in a yield of 35% with not more than 1% of other isomers.

(Z)-1-Octenyltriethylsilane

$^1$H-NMR (CDCl$_3$): δ 0.61 (q, 6H), 0.89 (t, 3H), 0.94 (t, 9H), 1.28 (m, 8H), 2.10 (q, 2H), 5.38 (td, J=14, 1 Hz, 1H), 6.37 (td, J=14, 7 Hz, 1H), (E)-1-Octenyltriethylsilane $^1$H-NMR (CDCl$_3$): δ 0.61 (q, 6H), 0.94 (t, 9H), 0.89 (t, 3H), 1.28 (m, 8H), 2.10 (q, 2H), 5.53 (td, J=19, 1 Hz, 1H), 6.03 (td, J=19, 6 Hz, 1H),

What is claimed is:

1. A catalyst for hydrogenation, dehydrosilylation of ketones, or hydrosilylation of dienes or acetylenes, which comprises a complex represented by the formula:

$$A^+[M_2H(CO)_{10}]^-$$

wherein A$^+$ represents an alkali metal cation, an ammonium cation, an iminium cation, or a phosphonium cation; and M represents a chromium atom, a molybdenum atom, or a tungsten atom.

* * * * *